(12) United States Patent
Helms

(10) Patent No.: US 7,126,048 B2
(45) Date of Patent: Oct. 24, 2006

(54) MILLET CULTIVAR GG102

(76) Inventor: Ronnie Sloan Helms, 1010 S. Lowe St., Stuttgart, AR (US) 72160

(*) Notice: Subject to any disclaimer, the term of this patent is extended or adjusted under 35 U.S.C. 154(b) by 68 days.

(21) Appl. No.: 10/903,545

(22) Filed: Jul. 29, 2004

(65) Prior Publication Data

US 2006/0026722 A1 Feb. 2, 2006

(51) Int. Cl.
*A01H 5/00* (2006.01)
*A01H 5/10* (2006.01)
*A01H 1/00* (2006.01)

(52) U.S. Cl. .................................. 800/320; 800/260
(58) Field of Classification Search ............... 800/260, 800/320

See application file for complete search history.

(56) References Cited

OTHER PUBLICATIONS

USDA, ARS National Genetic Resources Program. Germplasm Resources Information Network-(GRIN). [Online Database]. *Echinochloa crus-galli* (L) var. Ames 1293 deposited Jan. 18, 1990.*
Elton Robinson, New barnyardgrass millet scores as waterfowl forage, Delta Farm Press, Sep. 5, 2003, PRIMEDIA Business Magazines and Media, Inc., United States.
R.D. Baker, Millet Production, College of Agriculture and Home Economics Publication Catalog, 2003, pp. 1-6, Guide A-414, New Mexico State University, United States.

* cited by examiner

*Primary Examiner*—David H. Kruse
*Assistant Examiner*—Keith O. Robinson
(74) *Attorney, Agent, or Firm*—Keisling Pieper & Scott PLC; Trent C. Keisling; David B. Pieper

(57) ABSTRACT

A novel millet cultivar, designated GG102, is disclosed. The invention relates to the seeds of millet cultivar GG102, to the plants of millet GG102 and to methods for producing a millet plant produced by crossing the cultivar GG102 with itself or another millet variety. The invention further relates to hybrid millet seeds and plants produced by crossing the cultivar GG102 with another millet cultivar.

7 Claims, No Drawings

MILLET CULTIVAR GG102

CROSS REFERENCES

None.

GOVERNMENT RIGHTS

None.

BACKGROUND OF THE INVENTION

The present invention relates to a new and distinctive millet cultivar, designated GG102. The term "millet" is applied to various grassy crops whose seeds are harvested for human food or animal feed. Compared to other cereal grains, millets are generally suited to less fertile soils and poorer growing conditions, such as intense heat and low rainfall and require shorter growing seasons.

The earliest recorded document about millet reports that it was a "holy plant" in China around 2800 BC. As an ancient staple of India, Egypt, and North Africa, millet was once dominant commodity; as wheat is today.

Millet is generally considered a minor crop in the U.S. because it has lost a great deal of importance as a cereal crop in favor of other cereal crops such as wheat and rice. However, millet is becoming more important in the U.S. due to its advantages as a rotational or cover crop as well as its use in the hunting industry when planted to attract wild foul, for example ducks and geese.

Millet prefers hot summers and is very drought-resistant once established, making it a great grain plant for most of North America, including the desert states. It will not thrive in the cool wet summers of the Pacific Northwest, British Columbia, or Northeastern Maine and Canada. In regions where summers are potentially cool and wet, millet should be planted in a sunny, well-protected location.

Millet can be grown as a sole crop, mixed crop or as an intercrop. Under traditional cropping systems, millets are largely grown as a component of mixed or intercropping patterns than as a sole crop. This is mainly because of the numerous advantages associated with the intercropping/mixed cropping systems.

Millets include five genera, *Panicum, Setaria, Echinochloa, Pennisetum*, and *Paspalum*, all of the tribe Paniceae; one genus, *Eleusine*, in the tribe Chlorideae; and one genus, *Eragrostis*, in the tribe Festuceae. The most important cultivated species of millet are foxtail (*Setaria italica*), pearl or cattail millet (*Pennisetum glaucum*), proso (*Panicum miliaceum*), Japanese barnyard millet (*Echinochola crusgalli*), finger millet (*Eleusine coracana*), browntop millet (*Panicum ramosum*), koda or ditch millet (*Paspalum scrobiculatum*), and teff millet (*Eragrostis tef*).

The present invention relates to *Echinochola crusgalli*, commonly know as Japanese Millet but also called barnyard millet or billion dollar grass. Japanese millet is grown principally as a forage grass. Japanese millet is usually grown as a late-season green feed in temperate climates with humid or sub-humid conditions. It makes the most rapid growth of all millets under favorable weather conditions, ordinarily producing ripe grain in 45 days after seeding. The ordinary growth habit of this annual grass is an erect plant 2–4 ft tall with a panicle inflorescence made up of 5–15 sessile erect branches. Spiklets are ordinarily brownish to purple and are borne on one side of each branch. Seeds are slightly longer than wide and are larger than those of barnyardgrass. Japanese millet makes its best growth on good soils. It is not ordinarily subject to major fungal diseases; it is susceptible to several species of head smuts.

Millets are generally grown on less fertile soils. All millets respond to nitrogen and phosphorus fertilizers, but there are only broad guidelines on fertility practices for millets. Nitrogen requirements for heavy forage production and heavy grazing will likely be double those required for hay or seed crops. Phosphorus requirements will also be higher than those for hay or seed crops. Nutrient requirements include potassium, sulfur, calcium, magnesium, iron, copper, boron, manganese, zinc, molybdenum, and chlorine. One or more of these nutrients may be limiting in the less fertile soils used by millet producers.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Various recurrent selection techniques were used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, overall value of the advanced breeding lines, and number of successful cultivars produced per unit of input.

Promising advanced breeding lines are tested and compared to appropriate standards in environments representative of the target area. The best lines are candidates for new commercial cultivars; those still deficient in a few traits may be used as parents to produce new populations for further selection.

Development of new cultivars is a time-consuming process that requires precise forward planning, efficient use of resources, and a minimum of changes in direction.

One method of identifying a superior plant is to observe its performance relative to other cultivars. If a single observation is inconclusive, replicated observations provide a better estimate of its genetic worth.

The goal of plant breeding is to develop new, unique and superior millet cultivars and hybrids. The breeder initially selects and crosses two or more parental lines, followed by self-pollination and selection, producing many new genetic combinations. The breeder has no direct control at the cellular level; therefore, two breeders will not develop the same line, or even very similar lines, having the exact same traits.

The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new millet cultivars.

Pedigree breeding is used commonly for the improvement of self-pollinating crops. Two parents which possess favorable, complementary traits are crossed to produce an F1. An F2 population is produced by selfing one or several F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

In a multiple-seed procedure, millet breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Despite the importance of millets, production has remained low. Low yields of millets are generally attributed to lack of high yielding hybrids and to the fact that these crops are largely grown as rainfed crops.

SUMMARY OF THE INVENTION

The present invention is a novel millet cultivar designated GG102 with high yield potential, strong stalks, short maturity and can re-seed itself the following year. This invention thus relates to the seeds of millet cultivar GG102, to the plants of millet cultivar GG102 and to methods for producing a millet plant by crossing of the cultivar GG102 with itself or with another millet line.

The invention further relates to seeds of cultivar GG102 further comprising one or more specific, single gene traits. The invention also relates to plants of cultivar GG102 further comprising one or more specific, single gene traits. The invention includes methods for producing a millet plant by crossing the millet plant of cultivar GG102 further comprising one or more specific, single gene traits with itself or with another millet genotype.

Further, both first and second parent millet plants may be from the millet cultivar GG102. Therefore, any methods using the millet cultivar GG102 are part of this invention: selfing, backcrosses, hybrid breeding and crosses to populations. All plants produced using millet cultivar GG102 as a parent are within the scope of the invention.

DEFINITIONS

In the description and tables that follow, a number of terms are used. In order to provide a clear and consistent understanding of the specification and claims, including the scope to be given such terms, the following definitions are provided:

Maturity Date. Plants are considered mature when 95% of the pods have reached their mature color.

Plant Height. Plant height is taken from the top of soil to top of node of the plant and is measured in centimeters.

Grain Yield. Grain yield is measured in pounds per acre of harvested seed.

Grain Length (L). Length of a millet grain is measured in millimeters.

100 Grain Wt. The weight of 100 millet grains as measured in grams.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

DETAILED DESCRIPTION OF THE INVENTION

Millet cultivar GG102 is a high yielding, late maturing, premium quality long-grain millet variety that was evaluated from 2001–2003.

The cultivar has shown uniformity and stability, as described in the following variety description information. It has been self-pollinated a sufficient number of generations with careful attention to uniformity of plant type. The line has been increased with continued observation for uniformity.

Millet Cultivar GG102 has the following morphologic and other characteristics (based primarily on data collected at Stuttgart, Ark.).

Variety Description Information

Maturity (Arkansas County, Ark.)

Days to maturity: 55–75 days, grass emerging in April/May will mature in a 55–60 day period and grass emerging in July/August/September will mature in 60–75 days.

Culm: 25–130 cm tall, densely tufted, nodes glabrous

Blades: lax to drooping, 7–30 long, glabrous but with veins retrorsely scaberulous above, glabrous beneath, long acuminate and firm apiculate, margins retrorsely scaberulous.

Sheaths: glabrous, ligules absent.

Panicles: 6–24 cm long, to 3.5 com broad, lax, horizontal to prominently drooping at maturity, longest individual racemes 2.5–6 cm long, usually appressed to rachises, simple or branched, glabrous or sparsely hispid.

Spikelets: 3.8–6.5 mm long, 1.8–2.3 mm wide, ovate to ovate-elliptical, acuminate, in two irregular rows on each raceme, disarticulating at maturity.

First Glume: ¼–⅖ as long as spikelets

Second Glume: subequal to spikelets

Lower Florets: sterile

Lower Lemmas: usually equal in size to spikelets

Lower Paleas: well developed

Upper Lemmas: 3.5–4.5 mm, similar in length and width to upper glumes, ovate to broadly elliptic Grain Length: 1.8–2.5 mm long Grain Weight: 0.35–0.45 grams per 100 grains Grain Color: whitish to tan or light brown, lustrous Plant height and productivity variable, depending on soil fertility and available moisture.

Grain Yield: 2000 lbs/acre (Arkansas County, Ark.)

This invention is also directed to methods for producing a millet plant by crossing a first parent millet plant with a second parent millet plant, wherein the first or second millet plant is the millet plant from the line GG102. Further, both first and second parent millet plants may be from the cultivar GG102. Therefore, any methods using the cultivar GG102 are part of this invention: selfing, backcrosses, hybrid breeding, and crosses to populations. Any plants produced using cultivar GG102 as a parent are within the scope of this invention.

As used herein, the term "plant" includes plant cells, plant protoplasts, plant cells of tissue culture from which millet plants can be regenerated, plant calli, plant clumps, and plant cells that are intact in plants or parts of plants, such as pollen, flowers, embryos, ovules, seeds, pods, leaves, stems, anthers and the like. Thus, another aspect of this invention is to provide for cells which upon growth and differentiation produce a cultivar having essentially all of the physiological and morphological characteristics of GG102.

Culture for expressing desired structural genes and cultured cells are known in the art. Also as known in the art, millet is transformable and regenerable such that whole plants containing and expressing desired genes under regulatory control may be obtained.

This invention also is directed to methods for producing a millet plant by crossing a first parent millet plant with a second parent millet plant wherein either the first or second parent millet plant is a millet plant of the line GG102. Further, both first and second parent millet plants can come from the millet cultivar GG102. Still further, this invention also is directed to methods for producing a millet cultivar GG102-derived millet plant by crossing millet cultivar GG102 with a second millet plant and growing the progeny seed, and repeating the crossing and growing steps with the millet cultivar GG102-derived plant from 0 to 7 times. Thus, any such methods using the millet cultivar GG102 are part of this invention: selfing, backcrosses, hybrid production, crosses to populations, and the like. All plants produced using millet cultivar GG102 as a parent are within the scope of this invention, including plants derived from millet cultivar GG102. Advantageously, the millet cultivar is used in crosses with other, different, millet cultivars to produce first generation (F.sub.1) millet seeds and plants with superior characteristics.

As used herein, the term plant includes plant cells, plant protoplasts, plant cell tissue cultures from which millet plants can be regenerated, plant calli, plant clumps and plant cells that are intact in plants or parts of plants, such as embryos, pollen, ovules, leaves, husks, stalks, roots, root tips, anthers and the like.

The utility of millet cultivar GG102 also extends to crosses with other species. Common species used include:, *Panicum, Setaria, Echinochloa, Pennisetum*, and *Paspalum*, all of the tribe Paniceae; one genus, *Eleusine*, in the tribe Chlorideae; and one genus, *Eragrostis*, in the tribe Festuceae. The most important cultivated species of millet are foxtail (*Setaria italica*), pearl or cattail millet (*Pennisetum glaucum*), proso (*Panicum miliaceum*), Japanese barnyard millet (*Echinochola crusgalli*), finger millet (*Eleusine coracana*), browntop millet (*Panicum ramosum*), koda or ditch millet (*Paspalum scrobiculatum*), and teff millet (*Eragrostis tef*).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed cultivar.

Deposit Information

Applicants have made a deposit on Aug. 3, 2004 of at least 2500 seeds of the cultivar of the present invention in conformity with requirements with the American Type Culture Collection (ATCC), 10801 University Boulevard, Manassas, Va., 20110-2209 U.S.A., ATCC Accession Number No: PTA-6141. This deposit of cultivar GG102 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§ 1.801–1.809, including providing an indication of the viability of the sample. Applicant imposes no restrictions on the availability of the deposited material from the ATCC following issuance of the patent; however, Applicants have no authority to waive any restrictions imposed by law on the transfer of biological material or its transportation in commerce.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A millet seed of the cultivar designated GG102, wherein a representative sample of said seed has been deposited under ATCC Accession No. PTA-6141.

2. A millet plant, or a part thereof, of cultivar GG102, wherein a representative sample of seed of said cultivar has been deposited under ATCC Accession No. PTA-6141.

3. Pollen of the plant of claim 2.

4. An ovule of the plant of claim 2.

5. A millet plant, or a part thereof, having all of the physiological and morphological characteristics of the millet plant of claim 2.

6. A seed of the plant according to claim 2 or 5, wherein the seed is produced by crossing the plant with itself.

7. A method for producing a millet seed comprising crossing a first parent millet plant with a second parent millet plant and harvesting the resultant hybrid millet seed, wherein said first or second parent millet plant is cultivar GG102, a representative sample of seed of said cultivar has been deposited under ATCC Accession No. PTA-6141.

* * * * *